United States Patent
Takeuchi et al.

(10) Patent No.: US 9,676,688 B2
(45) Date of Patent: Jun. 13, 2017

(54) METHOD FOR PRODUCING 1,1-DICHLORO-3,3,3-TRIFLUOROPROPANE

(71) Applicant: ASAHI GLASS COMPANY, LIMITED, Chiyoda-ku (JP)

(72) Inventors: Yu Takeuchi, Chiyoda-ku (JP); Shoji Furuta, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 15/370,352

(22) Filed: Dec. 6, 2016

(65) Prior Publication Data

US 2017/0081264 A1    Mar. 23, 2017

Related U.S. Application Data

(63) Continuation of application No. PCT/JP2015/064933, filed on May 25, 2015.

(30) Foreign Application Priority Data

Jun. 6, 2014   (JP) .................................. 2014-117747

(51) Int. Cl.
| | | |
|---|---|---|
| C07C 17/278 | (2006.01) | |
| C07C 19/08 | (2006.01) | |
| C07C 19/10 | (2006.01) | |
| C07C 17/272 | (2006.01) | |

(52) U.S. Cl.
CPC .......... C07C 17/278 (2013.01); C07C 17/272 (2013.01); C07C 19/08 (2013.01); C07C 19/10 (2013.01)

(58) Field of Classification Search
CPC ..... C07C 17/272; C07C 17/278; C07C 19/08; C07C 19/10
See application file for complete search history.

(56) References Cited

U.S. PATENT DOCUMENTS 5,608,126 A    3/1997   Morikawa et al.

FOREIGN PATENT DOCUMENTS

| JP | 4-193841 | 7/1992 |
| JP | 8-73385 | 3/1996 |
| JP | 3484824 | 1/2004 |
| WO | WO 2014/175403 A1 | 10/2014 |

OTHER PUBLICATIONS

International Search Report issued Aug. 11, 2015 in PCT/JP2015/064933, filed on May 25, 2015.
T. Tanuma et al., "19F nuclear magnetic resonance studies of halogenated propanes", Journal of Flourine Chemistry, vol. 57, 022-1139/92, pp. 26.

*Primary Examiner* — Jafar Parsa
(74) *Attorney, Agent, or Firm* — Oblon, McClelland, Maier & Neustadt, L.L.P.

(57) ABSTRACT

To provide a method for obtaining 1,1-dichloro-3,3,3-trifluoropropane by reacting 1,1-difluoroethylene with dichlorofluoromethane, which suppresses the production of chloroform as a by-product and achieves a product having a high R-243fa concentration. This method is characterized by obtaining 1,1-dichloro-3,3,3-trifluoropropane by reacting 1,1-difluoroethylene with dichlorofluoromethane in the presence of trifluoromethane.

14 Claims, No Drawings

METHOD FOR PRODUCING 1,1-DICHLORO-3,3,3-TRIFLUOROPROPANE

This application is a continuation of PCT Application No. PCT/JP2015/064933, filed on May 25, 2015, which is based upon and claims the benefit of priority from Japanese Patent Application No. 2014-117747 filed on Jun. 6, 2014. The contents of those applications are incorporated herein by reference in their entireties.

TECHNICAL FIELD

The present invention relates to a method for producing 1,1-dichloro-3,3,3-trifluoropropane (refrigerant number: R-243fa).

BACKGROUND ART

In this specification, abbreviated names (such as a refrigerant number) of halogenated hydrocarbon compounds are described in brackets after the compound names in some cases. And in this specification, the abbreviated names are employed instead of the compound names as the case requires.

R-243fa, which is a raw material for trans-1-chloro-3,3,3-trifluoropropene (hereinafter, referred to also as R-1233zd(E)) to be used as e.g. a refrigerant, is an industrially useful compound or intermediate. R-1233zd(E) is recently promising as an alternative compound to 1,1,1,2-tetrafluoroethane and 1,1,1,3,3-pentafluoropropane which are greenhouse gases.

A method for producing R-243fa may, for example, be a method of reacting 1,1-difluoroethylene (vinylidene fluoride, hereinafter, referred to also as VdF) with dichlorofluoromethane (refrigerant number: R-21) in the presence of a Lewis acid catalyst (Patent Document 1).

PRIOR ART DOCUMENT

Patent Document

Patent Document 1: JP-A-8-73385

DISCLOSURE OF INVENTION

Technical Problem

In the method of reacting VdF with R-21, by-products such as chloroform (refrigerant number: R-20) are formed. In a case where R-243fa produced is used as a raw material for e.g. R-1233zd(E), by-products are preferably removed, and R-243fa produced is usually purified from a reaction product.

However, the boiling point of R-20 contained in the by-products is close to that of R-243fa, and therefore it is difficult to separate it from the product by distillation. Further, if additional purification procedures are needed to separate R-20, production of R-243fa will be cumbersome, whereby production efficiency will be low.

Moreover, in the method of reacting VdF with R-21, it is desired that the concentration of R-243fa in the product is high in view of reduction of the raw material cost and high production efficiency.

Under these circumstances, it is an object of the present invention to provide a method for obtaining R-243fa by reacting VdF with R-21, so as to reduce the amount of R-20 formed as a by-product and achieve a high concentration of R-243fa in the product.

Solution to Problem

The present invention provides a method for producing R-243fa having the following constructions [1] to [14].

[1] A method for producing R-243fa, which comprises reacting VdF with R-21 in the presence of trifluoromethane (refrigerant number: R-23), to obtain R-243fa.

[2] The method for producing R-243fa according to [1], wherein the amount of R-23 used relative to the amount of R-21 used, is from 10 ppm to 10% by molar ratio.

[3] The method for producing R-243fa according to [1], wherein the amount of R-23 used relative to the amount of VdF used, is from 10 ppm to 10% by molar ratio.

[4] The method for producing R-243fa according to any one of [1] to [3], wherein R-23 is continuously or intermittently supplied to the reaction system.

[5] The method for producing R-243fa according to any one of [1] to [4], wherein R-23 is present in the reactor before initiation of the reaction.

[6] The method for producing R-243fa according to any one of [1] to [5], wherein the ratio of VdF relative to R-21 is from 0.5 to 1.5 by molar ratio.

[7] The method for producing R-243fa according to any one of [1] to [6], wherein the reaction temperature is from −80 to 200° C.

[8] The method for producing R-243fa according to any one of [1] to [7], wherein the reaction is carried out in the presence of a catalyst.

[9] The method for producing R-243fa according to [8], wherein the catalyst is a Lewis acid catalyst.

[10] The method for producing R-243fa according to any one [1] to [9], wherein R-243fa and 1,3-dichloro-1,3,3-trifluoropropane (refrigerant number: R-243fb) are produced by the reaction.

[11] The method for producing R-243fa according to [10], wherein the proportion of R-243fa relative to the total amount (100 mol %) of R-243fa and R-243fb, is from 50 to 95 mol %.

[12] The method for producing R-243fa according to any one of [1] to [11], wherein the reaction is carried out in a liquid phase.

[13] The method for producing R-243fa according to [12], wherein the solvent in the reaction system is R-243fa.

[14] The method for producing R-243fa according to [13], wherein R-243fa is present in the reactor before initiation of the reaction, so as to form the liquid phase together with R-243fa produced by the reaction.

Advantageous Effects of Invention

According to the production method of the present invention, it is possible to reduce the amount of R-20 formed as a by-product and achieve a high concentration of R-243fa in the product.

DESCRIPTION OF EMBODIMENTS

<Method for Producing R-243Fa>

The method for producing R-243fa of the present invention is a method for obtaining R-234fa by reacting VdF with R-21 in the presence of R-23.

The reaction of VdF with R-21 is represented by the following formula (1):

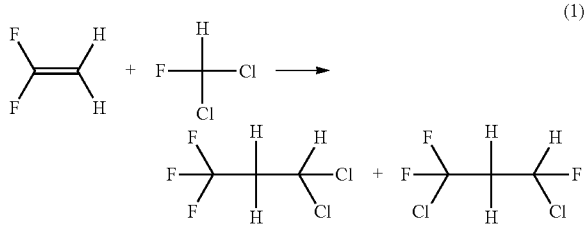

(1)

The product includes R-243fb in addition to R-243fa.

The proportions of R-243fa and R-243fb in the product vary depending upon reaction conditions such as reaction temperature and the type of a catalyst, but usually, the proportion of R-243fb is at least 5 mol % and at most 50 mol %, and the proportion of R-243fa is at least 50 mol % and at most 95 mol %, relative to 100 mol % as a total of R-243fa and R-243fb.

Further, the product includes e.g. R-20 or 1,1,1-trifluoroethane (refrigerant number: R-143a) in addition to R-243fa and R-243fb.

The reactor used in the reaction may be one commonly used in production of compounds.

VdF and R-21 as raw materials, and R-23 which is present in the reaction system, are industrially available at a low cost.

The reaction may be carried out in a gas phase or a liquid phase. In view of volume efficiency in the production, it is preferred to carry out the reaction in a liquid phase.

The reaction may be a batch type reaction or a continuous type reaction. In the case of the batch type reaction, VdF, R-21 or R-23 may be present in the reactor before initiation of the reaction, or may be continuously or intermittently supplied to the reaction system. Further, in a case where R-23 is continuously or intermittently supplied to the reaction system, R-23 may be supplied together with VdF or R-21.

The amount of VdF used relative to the amount of R-21 used is preferably from 0.5 to 1.5, more preferably from 0.8 to 1.2 by molar ratio.

The amount of R-23 used relative to the amount of R-21 used is preferably from 10 ppm to 10%, more preferably from 100 to 10,000 ppm, particularly preferably from 1,000 to 6,000 ppm by molar ratio. When the amount of R-23 used relative to the amount of R-21 used is at least the above lower limit value, it is possible to enhance the effect of suppressing the amount of by-products formed. On the other hand, when it is at most the above upper limit value, it is possible to reduce the amount of R-20 formed, and achieve a high concentration of R-243fa in the product.

The amount of R-23 used relative to the amount of VdF used is preferably from 10 ppm to 10%, more preferably from 100 to 10,000 ppm, particularly preferably from 1,000 to 6,000 ppm by molar ratio. When the amount of R-23 used relative to the amount of VdF used is at least the above lower limit value, it is possible to enhance the effect of suppressing the amount of by-products formed. On the other hand, when it is at most the above upper limit value, such is advantageous in view of volume efficiency of the reactor since the amount of the raw materials treated per unit time of the reactor will not drastically decrease.

The reaction temperature is preferably from −80 to 200° C., more preferably from −40 to 100° C., particularly preferably from −20 to 60° C., in view of suppression of side reaction and reaction rate.

The pressure in the reactor depends on the type of raw materials, but may be a normal pressure, elevated pressure or reduced pressure. In view of easiness of operation management, normal pressure or elevated pressure is preferred. Further, the gauge pressure is preferably from 0 to 2.0 MPa, more preferably from 0 to 1.0 MPa, particularly preferably from 0 to 0.6 MPa.

The reaction time is preferably from 0.1 minute to 24 hours, more preferably from one minute to 10 hours.

The reaction of VdF with R-21 is preferably carried out in the presence of a catalyst. The catalyst may, for example, be a Lewis acid catalyst.

The Lewis acid catalyst is preferably a halide or an oxyhalide of at least one element selected from a Group 13 element of B, Al, Ga and In, an iron group element of Fe, Ni and Co, a Group 4 element of Ti, Zr and Hf, a Group 5 element of Nb and Ta, Sb, Sn, and W. Particularly preferred is a halide or an oxyhalide of a Group 13, Group 4 or Group 5 element.

The halide catalyst is preferably a halide such as chloride, fluoride or chlorofluoride of B, Al, Ga, In, Fe, Ni, Co, Sb, Nb, Sn, Ti, Zr, Hf or W.

Specifically, e.g. $BF_3$, $AlCl_3$, $AlClF_2$, $GaCl_3$, $InCl_3$, $FeCl_3$, $NiCl_2$, $CoCl_2$, $SbF_5$, $SbCl_2F_3$, $NbCl_5$, $SnCl_2$, $TiCl_4$, $TiCl_2F_2$, $ZrCl_4$, $ZrCl_2F_2$, $ZrClF_3$, $HfCl_4$, $HfClF_3$, $WCl_6$ or $TaCl_5$ is preferred.

The oxyhalide catalyst is preferably produced by treating an oxide of only one type of the above element or a composite oxide of at least two of the above elements with a proper halogenating agent such as a chlorofluorocarbon such as trichlorofluoromethane (refrigerant number: R-11), dichlorodifluoromethane (refrigerant number: R-12) or 1,1,2-trichloro-1,2,2-trifluoroethane, a hydrochlorofluorocarbon such as R-21 or chlorodifluoromethane (refrigerant number: R-22), chlorine, hydrogen fluoride or fluorine.

Specifically, the oxide catalyst is preferably e.g. $Al_2O_3$, $ZrO_2$, $TiO_2$ or $Fe_2O_3$. It is considered that such an oxide catalyst is halogenated by e.g. R-21 so as to be converted into an oxyhalide catalyst in the reaction system.

The halide or oxyhalide catalyst of the above element may further contain another element such as at least one element of e.g. Si, Zn, Mg, Cr, Cu, V, Bi and Mo. In this case, such an element of e.g. Si, Zn, Mg, Cr, Cu, V, Bi or Mo is usually contained in the form of a halide or an oxyhalide.

The catalyst is preferably $AlCl_3$, modified $ZrCl_4$ treated with trichlorofluoromethane or the like, alumina, zirconium oxide, titanium oxide or $HfCl_4$, particularly preferably $AlCl_3$, modified $ZrCl_4$ treated with trichlorofluoromethane or the like, alumina or zirconium oxide, in view of availability and reaction rate.

The amount of the catalyst is preferably from 0.001 to 50 mass %, particularly preferably from 0.01 to 10 mass %, relative to the raw materials, although it depends on the type of the catalyst used.

The catalyst is preferably supplied to the reactor before initiation of the reaction. Further, in the case of a continuous type reaction, it is preferred that the catalyst is continuously or intermittently supplied to the reaction system together with the raw materials, and the catalyst is continuously taken out from the reaction system together with the product. In such a case, it is preferred that the catalyst taken out is recycled.

At the time of reacting VdF with R-21, an additive such as a solvent other than the above-mentioned R-23 and the catalyst, may be added. However, with a view to facilitating purification of R-243fa from the reaction product, the amount of an additive other than the reaction product as a solvent, is preferably small, and particularly preferably no additive is used.

In a case where the reaction is carried out in a liquid phase, the solvent is not particularly limited so long as VdF and R-21 as raw materials can be moderately dissolved therein. For example, R-243fa, R-243fb, perfluorooctane, perfluorobutyltetrahydrofuran, trichloropentafluoropropane (refrigerant number: R-215), dichloropentafluoropropane (refrigerant number: R-225), tetrachlorotetrafluoropropane (refrigerant number: R-224) or dichlorotrifluoropropane (refrigerant number: R-243) may be mentioned.

The solvent is preferably R-243fa. As the R-243fa used as the solvent, it is possible to use R-243fa obtained by the production method of the present invention. Further, it is possible to use, as the solvent, a reaction mixture produced by the production method of the present invention or a reaction mixture having the concentration of by-products reduced by purifying the reaction mixture. Especially, it is preferred that the R-243fa is present in the reactor before initiation of the reaction, so as to form the liquid phase together with R-243fa produced by the reaction. Here, the R-243fa which is present in the reactor before initiation of the reaction, may be R-243fa alone or R-243fa containing a by-product such as R-243fb.

R-243fa produced by the present invention may be obtained by purifying the reaction mixture produced. Further, in a case where R-243fa produced is used as a raw material for e.g. R-1233zd(E), R-243fa obtained by the present invention may contain a by-product to some extent, and in this case, such a reaction mixture may be purified to obtain a mixture with a more reduced concentration of the by-product and with a more increased concentration of R-243fa.

The purification method may, for example, be distillation, extractive distillation or adsorption. Among them, distillation is preferred in view of easiness.

The distillation may be carried out under normal pressure, elevated pressure or reduced pressure. The distillation is preferably carried out under normal pressure.

OTHER EMBODIMENTS

The method for producing R-243fa of the present invention is not limited to the above method so long as it is a method of reacting VdF with R-21 wherein R-23 is present in the reaction system.

For example, as VdF or R-21 as a raw material, an unreacted one taken out from the reaction system or one separated during the purification, may be recycled.

Further, as R-23, one contained in the above-mentioned raw materials, catalyst or additive, may be used other than a commercial product, or one taken out from the reaction system during or after the reaction or one separated during the purification, may be recycled.

<Application of R-243fa>

R-243fa produced by the present invention may be used for various applications, and it is particularly useful as a raw material for R-1233zd(E).

The process for producing R-1233zd(E) using R-243fa as a raw material is not particularly limited, and may be a known method, such as a method of dehydrochlorination of R-243fa in an alkali solution (J. Am. Chem. Soc., volume 64, 1942, pp. 1157-1159), or a method of dehydrochlorination of R-243fa in the presence of a metal catalyst (U.S. Pat. No. 8,653,309).

R-1233zd(E) is useful as a refrigerant, a blowing agent, a foam, a prefoam mix, a solvent, a detergent, a propellant or a compatibilizer, or a raw material monomer or a synthetic intermediate for a functional material.

EXAMPLES

Now, the present invention will be described in detail with reference to Examples, but it should be understood that the present inventions is by no means restricted thereto.

<Raw Materials>

R-23: "Asahi Fron-23" manufactured by Asahi Glass Company, Limited.

VdF: "Vinylidene fluoride" manufactured by KUREHA CORPORATION.

R-21: "Dichlorofluoromethane" manufactured by Asahi Glass Company, Limited.

Catalyst: "Zirconium(IV) Chloride 98% anhydrous" manufactured by ACROS ORGANIC K.K.

Example 1

Before initiation of the reaction, 1,001 g of an initial solvent (composition: R-243fa: 67.9 mol %, R-243fb: 8.3 mol %, R-20: 1.3 mol %, R-21: 1.4 mol %, other component: 21.1 mol %) (hereinafter, simply referred to also as an initial solvent), 7,218 g of R-21 and 78.0 g of the catalyst, were charged into an autoclave (material: SUS, capacity: 10 L) (hereinafter referred to also as a reactor).

Then, while maintaining the reaction temperature in the reactor to be from 0 to 5° C. and stirring (stirring vane: "Fullzone (registered trademark)" manufactured by Kobelco Eco-Solutions Co., Ltd., number of revolution: 200 rpm) the reaction fluid, VdF and R-23 were supplied continuously respectively at 2,500 NmL/min and 10 NmL/min so as to carry out the reaction. Here, the amount of VdF and the amount of R-23 used, supplied during the reaction, were respectively 4,458 g and 6,270 NmL (19.59 g).

After termination of the supply of VdF and R-23, the reaction fluid was further stirred for 30 minutes, and then the gas phase portion was replaced with nitrogen so as to complete the reaction. The reaction time was 10 hours and 57 minutes.

After completion of the reaction, the reaction crude fluid was discharged from the bottom of the reactor, with stirring. The amount of the reaction crude fluid was 12,543 g. This reaction crude fluid was subjected to composition analysis by a gas chromatograph (column: "GC column DB-1" manufactured by Agilent technologies K.K. (length 60 m×inner diameter 250 μm×thickness 1 μm)).

Example 2

Before initiation of the reaction, 1,001 g of the initial solvent, 7,215 g of R-21, 6,000 NmL (18.75 g) of R-23 and 73.7 g of the catalyst were charged into the same reactor as in Example 1.

Then, while maintaining the reaction temperature in the reactor to be from 0 to 5° C. and stirring the reaction fluid in the same manner as in Example 1, VdF was supplied continuously at 2,500 NmL/min so as to carry out the reaction. Here, the amount of VdF added during the reaction was 4,506 g.

After termination of the supply of VdF, the reaction fluid was further stirred for 30 minutes, and then the gas phase portion was replaced with nitrogen so as to complete the reaction. The reaction time was 10 hours and 58 minutes.

After completion of the reaction, the reaction crude fluid was discharged from the bottom of the reactor, with stirring. The amount of the reaction crude fluid was 12,520 g. This reaction crude fluid was subjected to composition analysis in the same manner as in Example 1.

Comparative Example 1

Before initiation of the reaction, 1,130 g of the initial solvent, 7,202 g of R-21 and 78.1 g of the catalyst were charged into the same reactor as in Example 1.

Then, while maintaining the reaction temperature in the reactor to be from 0 to 5° C. and stirring the reaction fluid in the same manner as in Example 1, VdF was supplied continuously at 2,500 NmL/min so as to carry out the reaction. Here, the amount of VdF added during the reaction was 4,480 g.

After termination of the supply of VdF, the reaction fluid was further stirred for 30 minutes, and then the gas phase portion was replaced with nitrogen so as to complete the reaction.

After completion of the reaction, the reaction crude fluid was discharged from the bottom of the reactor, with stirring. The amount of the reaction crude fluid was 12,822 g. This reaction crude fluid was subjected to compositional analysis in the same manner as in Example 1.

The reaction conditions in Examples 1 and 2 and Comparative Example 1 and the results of compositional analysis of the reaction crude fluid obtained are shown in the following Table 1.

TABLE 1

| | | Example 1 | Example 2 | Comparative Example 1 |
|---|---|---|---|---|
| Reaction conditions | Reaction temperature (° C.) | 0 to 5 | 0 to 5 | 0 to 5 |
| | Number of revolution (rpm) | 200 | 200 | 200 |
| | Amount of R-21 used (g) | 7,218 | 7,215 | 7,202 |
| | VdF supply rate (NmL/min) | 2,500 | 2,500 | 2,500 |
| | Amount of VdF used (g) | 4,458 | 4,506 | 4,480 |
| | R-23 initial supply amount (NmL) | — | 6,000 | — |
| | R-23 supply rate (NmL/min) | 10 | — | — |
| | Amount of R-23 used (g) | 19.59 | 18.75 | — |
| | R-23/R-21 (molar ratio) (ppm) | 3,994 | 3,824 | — |
| | R-23/VdF (molar ratio) (ppm) | 4,018 | 3,804 | — |
| Results of compositional analysis (mol %) | $CHF_3$ (R-23) | 0.00 | 0.00 | 0.00 |
| | $CH_2=CF_2$ (VdF) | 0.00 | 0.06 | 0.62 |
| | $CH_3CF_3$ (R-143a) | 3.15 | 1.92 | 3.55 |
| | $CHClF_2$ (R-22) | 0.03 | 0.02 | 0.07 |
| | $CHCl_2F$ (R-21) | 2.21 | 1.78 | 3.10 |
| | $CF_3CH_2CHClF$ (R-244fa) | 0.35 | 0.33 | 0.35 |
| | $CF_3CH_2CHCl_2$ (R-243fa) | 67.26 | 69.24 | 65.31 |
| | $CClF_2CH_2CHClF$ (R-243fb) | 9.19 | 10.45 | 8.82 |
| | $CHCl_3$ (R-20) | 1.05 | 0.93 | 1.73 |
| | Other high boiling products | 16.76 | 15.27 | 16.45 |
| | R-20/R243fa (mol %) | 1.57 | 1.34 | 2.65 |

As the above results of compositional analysis, the content of R-243fa in the reaction crude fluid was high in each of Examples 1 and 2 where R-23 was added to the reaction system, as compared with Comparative Example 1 where no R-23 was added.

Further, the proportions of R-20, R-21 and R-143a in the reaction crude fluid were low in each of Examples 1 and 2 where R-23 was added to the reaction system, as compared with Comparative Example 1 where no R-23 was added.

INDUSTRIAL APPLICABILITY

The production method of the present invention is a method of reacting VdF with R-21, which can be suitably employed for mass production of R-243fa since the concentration of by-products such as R-20 in the product is low and the concentration of R-243fa is high. R-243fa obtained by the production method of the present invention can be used as a raw material for e.g. R-1233zd(E).

What is claimed is:

1. A method for producing 1,1-dichloro-3,3,3-trifluoropropane, which comprises reacting 1,1-difluoroethylene with dichlorofluoromethane in the presence of trifluoromethane, to obtain 1,1-dichloro-3,3,3-trifluoropropane.

2. The method for producing 1,1-dichloro-3,3,3-trifluoropropane according to claim 1, wherein the amount of trifluoromethane used relative to the amount of dichlorofluoromethane used, is from 10 ppm to 10% by molar ratio.

3. The method for producing 1,1-dichloro-3,3,3-trifluoropropane according to claim 1, wherein the amount of trifluoromethane used relative to the amount of 1,1-difluoroethylene used, is from 10 ppm to 10% by molar ratio.

4. The method for producing 1,1-dichloro-3,3,3-trifluoropropane according to claim 1, wherein trifluoromethane is continuously or intermittently supplied to the reaction system.

5. The method for producing 1,1-dichloro-3,3,3-trifluoropropane according to claim 1, wherein trifluoromethane is present in the reactor before initiation of the reaction.

6. The method for producing 1,1-dichloro-3,3,3-trifluoropropane according to claim 1, wherein the ratio of 1,1-difluoroethylene relative to dichlorofluoromethane is from 0.5 to 1.5 by molar ratio.

7. The method for producing 1,1-dichloro-3,3,3-trifluoropropane according to claim 1, wherein the reaction temperature is from −80 to 200° C.

8. The method for producing 1,1-dichloro-3,3,3-trifluoropropane according to claim 1, wherein the reaction is carried out in the presence of a catalyst.

9. The method for producing 1,1-dichloro-3,3,3-trifluoropropane according to claim 8, wherein the catalyst is a Lewis acid catalyst.

10. The method for producing 1,1-dichloro-3,3,3-trifluoropropane according to claim 1, wherein 1,1-dichloro-3,3,3-trifluoropropane and 1,3-dichloro-1,3,3-trifluoropropane are produced by the reaction.

11. The method for producing 1,1-dichloro-3,3,3-trifluoropropane according to claim 10, wherein the proportion of 1,1-dichloro-3,3,3-trifluoropropane relative to the total amount (100 mol %) of 1,1-dichloro-3,3,3-trifluoropropane and 1,3-dichloro-1,3,3-trifluoropropane, is from 50 to 95 mol %.

12. The method for producing 1,1-dichloro-3,3,3-trifluoropropane according to claim 1, wherein the reaction is carried out in a liquid phase.

13. The method for producing 1,1-dichloro-3,3,3-trifluoropropane according to claim 12, wherein the solvent in the reaction system is 1,1-dichloro-3,3,3-trifluoropropane.

14. The method for producing 1,1-dichloro-3,3,3-trifluoropropane according to claim 13, wherein 1,1-dichloro-3,3,3-trifluoropropane is present in the reactor before initiation of the reaction, so as to form the liquid phase together with 1,1-dichloro-3,3,3-trifluoropropane produced by the reaction.

* * * * *